United States Patent [19]

Bochner et al.

[11] Patent Number: 4,680,262
[45] Date of Patent: Jul. 14, 1987

[54] PERIPLASMIC PROTEIN RECOVERY

[75] Inventors: Barry R. Bochner, Alameda; Kenneth C. Olson, Burlingame; Rong-Chang Pai, Foster City, all of Calif.

[73] Assignee: Genentech, Inc., South San Francisco, Calif.

[21] Appl. No.: 658,339

[22] Filed: Oct. 5, 1984

[51] Int. Cl.$^4$ .................... C12P 21/00; C12N 15/00; C12N 1/06
[52] U.S. Cl. .................... 435/68; 435/172.3; 435/317; 435/259; 435/803; 935/48
[58] Field of Search .................... 435/68, 172.3, 317, 435/803, 804, 259; 935/40, 41, 47, 48

[56] References Cited

U.S. PATENT DOCUMENTS

| | | | |
|---|---|---|---|
| 4,275,166 | 6/1981 | McCollough et al. | 435/259 |
| 4,497,730 | 2/1985 | Ames et al. | 435/68 |

FOREIGN PATENT DOCUMENTS

| | | | |
|---|---|---|---|
| 0022242 | 1/1981 | European Pat. Off. | 435/172.3 |
| 0048970 | 4/1982 | European Pat. Off. | 935/41 |
| 0061250 | 9/1982 | European Pat. Off. | 435/259 |
| 0112012 | 6/1984 | European Pat. Off. | 435/172.3 |
| 0111389 | 6/1984 | European Pat. Off. | 435/172.3 |
| 0114695 | 8/1984 | European Pat. Off. | 435/172.3 |
| WO84/00774 | 3/1984 | PCT Int'l Appl. | 435/172.3 |
| 2033905 | 5/1980 | United Kingdom | 935/40 |

OTHER PUBLICATIONS

Davis, B. D. and R. Dulbecco "Sterilization and Disinfection" In: Davis, B. D. et al. *Microbiology,* 3rd ed, (New York, Harpes and Row, 1980) pp. 1264–1274.
Bungay, H. R. et al., "Biochemical Engineering" In: Perry, R. H., et al., *Perry's Chemical Engineers Handbook,* 6th ed. (New York, McGraw-Hill) pp. 27-1-2-7-19.
McGregor, W. C. "Large-Scale Isolation and Purification of Proteins from Recombinant E. Coli" In: Venkatasubramanian, K. et al., *Biochemical Engineering III,* (New York, New York Academy of Sciences, 1983) pp. 231–237.
Inouye et al., "J. Bact." 149(2):434–439 (Feb. 1982).
Picken et al., "Infection and Immunity" 42(1):269–275 (Oct. 1983).
Michaelis et al., "J. Bact." 154(1):366–374 (Apr. 1983).
Miyake et al., "J. Biochem." 97:1429–1436 (1985).
Saier, M. H. "The Bacteria" VII (4) 218–222.
Atlan et al., "Appl. Microb. Biotechnol." 19:5–12 (1984).
Wanner, B. L. "J. Mol. Biol." 166:283–308 (1983).
Calcott et al., "Can. J. Microbiol." 30:339–344 (1984).
MacLeod et al., "Symp. Soc. Gen. Microbiol." 26:81–109 (1976).
Neu et al., "J. Biol. Chem." 240(9):3685–3692 (1965).

*Primary Examiner*—Thomas G. Wiseman
*Assistant Examiner*—Karen Maurey

[57] ABSTRACT

Periplasmic proteins are recovered from transformed gram negative bacteria by a process comprising freezing and thawing the cells. Advantages are obtained by culturing the cells in phosphate-limiting media and by killing the cells prior to separation of periplasmic proteins.

24 Claims, 12 Drawing Figures

THE ST II GENE

```
TAAATACCTACAACGGGTGATTGACACTACACTCATTAACTATGCAAGTAGCATTAAAAATCTTAATAAAGGAGAGC
1                   20                  40                  60                  80
                -35                             -10                      MnII    S.D.
TTCGTCACATTTTTTGACTTGACTCATATAAAAGCCCACTGGTATAAGTTTATTGCTTATAGCAATAAGGTTGAGGTG
         ATTTT                                                                160
                                                           100                 120                 140
                                                                                        -10
        met lys asn ile ala phe leu leu ala ser met phe val phe ser ile ala
        ATG AAA AAG AAT ATC GCA TTT CTT CTT GCA TCT ATG TTC GTT TTT TCT ATT GCT
                                            180                     200
                        -1 cleavage site                                    10
thr asn ala tyr ala SER THR GLN SER ASN LYS LYS ASP LEU CYS GLU HIS TYR ARG GLN
ACA AAT GCC TAT GCA TCT ACA CAA TCA AAT AAA GAT CTG TGT GAA CAT TAT AGA CAA
220                         240                         260
                                                BglII
                20                                      30
ILE ALA LYS GLU SER CYS LYS LYS GLY PHE LEU GLY VAL ARG ASP GLY THR ALA GLY ALA
ATA GCC AAG GAA AGT TGT AAA AAA GGT TTT TTA GGG GTT AGA GAT GGT ACT GCT GGA GCA
280                         300                         320
                                                        RsaI
        40
CYS PHE GLY ALA GLN ILE MET VAL ALA ALA LYS GLY CYS OC
TGC TTT GGC GCC CAA ATA ATG GTT GCA GCA AAA GGA TGC TAA TATATTTATCAATAGCATTCAGCA
340                         360                         380                         400

CCATATACACAAAAATAATTTTTCATAAAAAGAACTCTATAAAATAAATATTTTTTGTGACAATGTCCTAACGCAAGACG
420                         440                         460                         480

GACATTGTCCATTTCTCACTGCAGGTAAATGATCTGTAAATAGTC
                500 PstI      520
```

Fig.1.

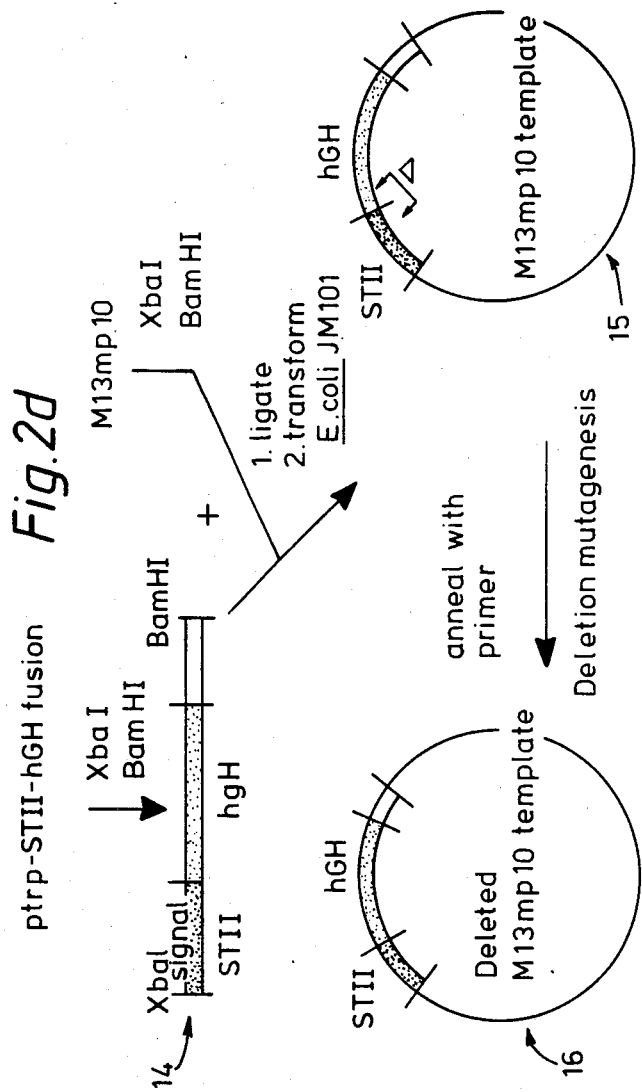

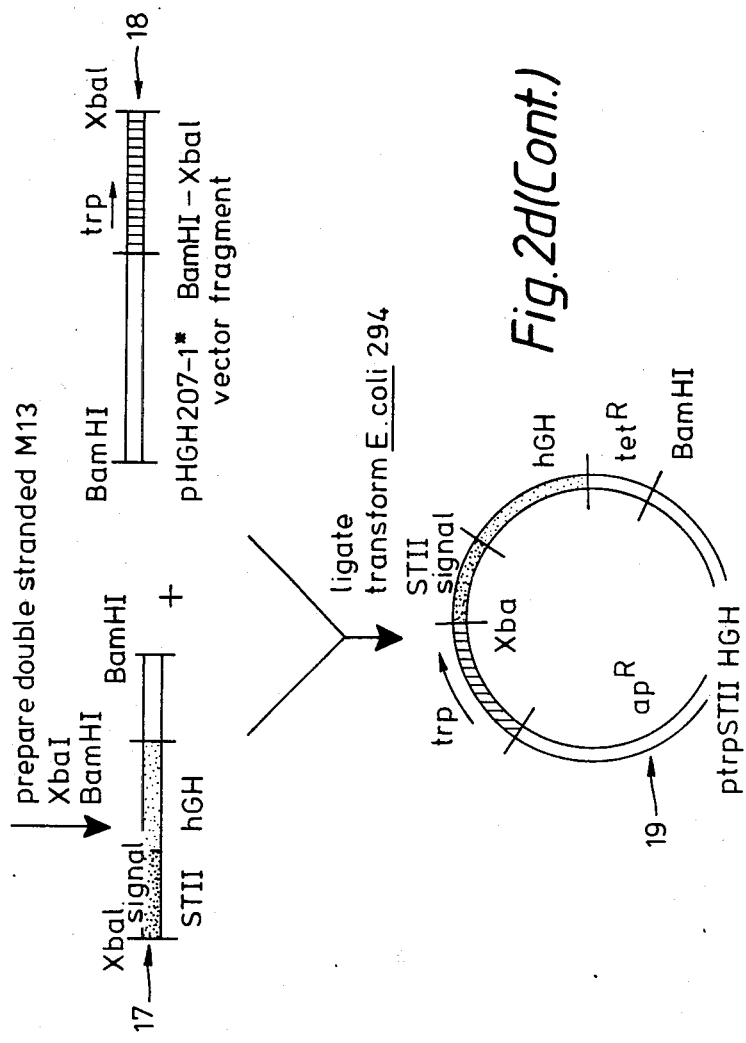

Fig. 3A.

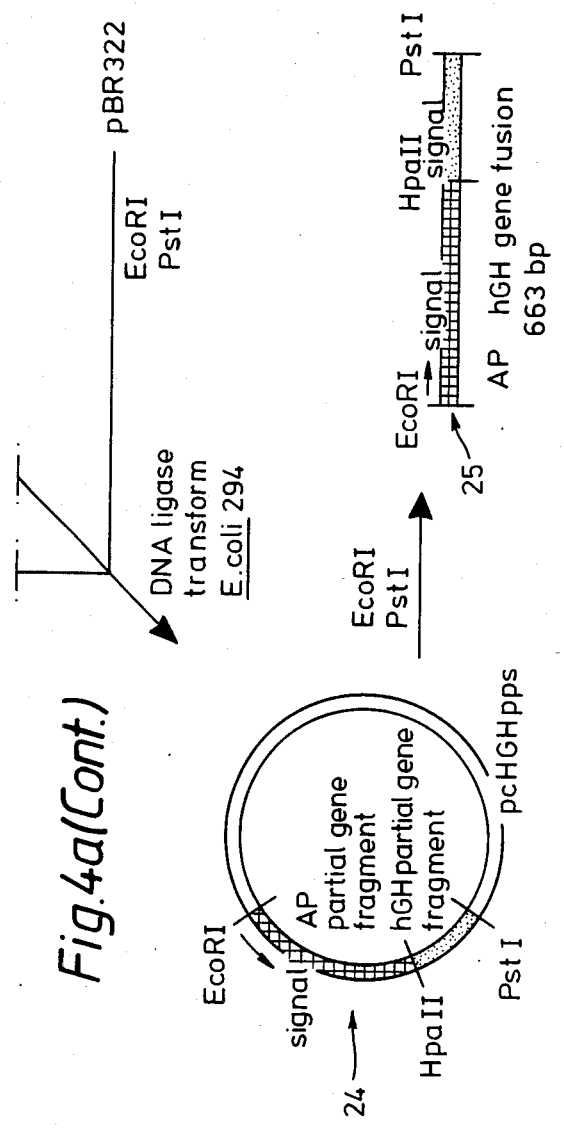

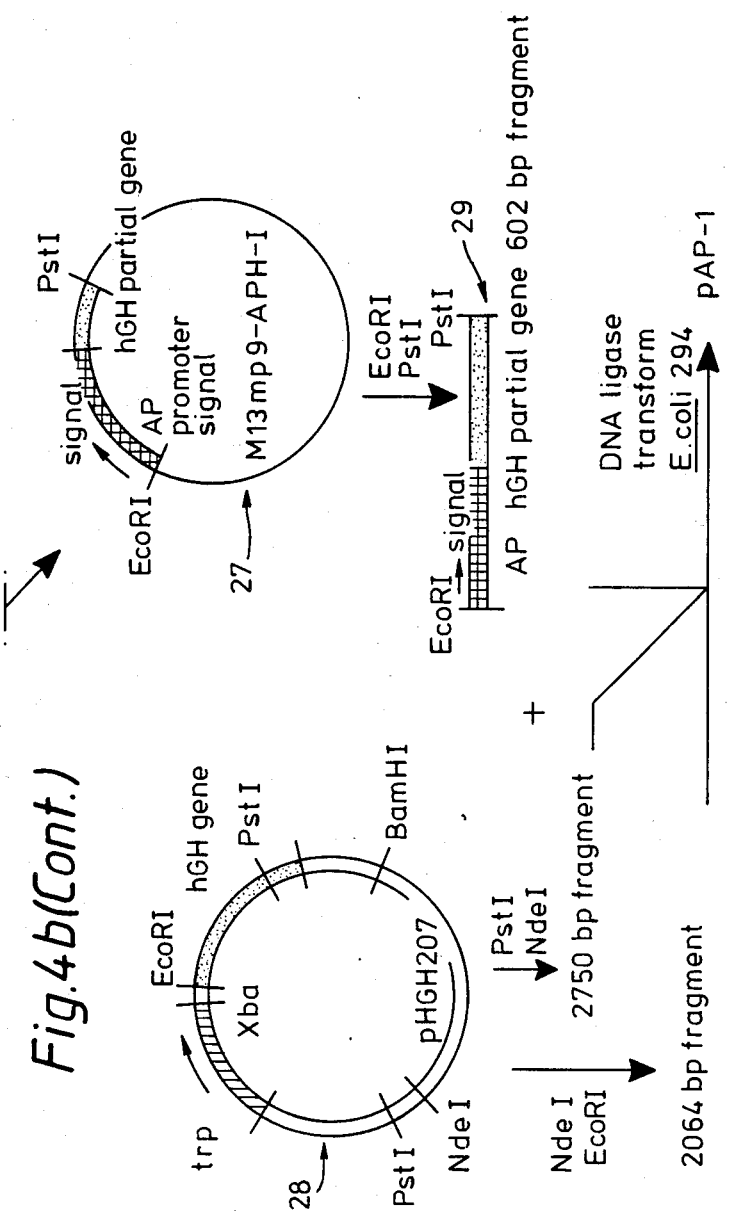

```
GAATTCAACTTCTCTCCATACTTTGGATAAGGAATACAGACATGAAAAATCTCATTGCTGAGTGTGTTATTTAAGCTTGCC

CAAAAAGAAGAAGAGTCGAAAGAACTGTGTGCCCAGGTAGAAGCTTTGGAGATTATCGTCACTGCAATGCTTCGCAATA

TGGCGCAAAATGACCAACAGCGGTTGATTGATCAGGTAGAGGGGCGCTGTACGAGGTAAAGCCCGATGCCAGCATTCC

TGACGACGATACGGAGCTGCTGCGCGATTACGTAAAAGAAGTTATTGAAGCATCCTCGTCAGTAAAAAGTTAATCTTTC

AACAGCTGTCATAAAGTTGTCACGGGCCGAGACTTATAGTCGCTTTGTTTTTATTTTTAATGTATTGTAACTAGTACG
                                              -23          -20
     trp S.D.          STII S.D.        met lys lys asn ile ala phe leu leu
CAAGTTCACGTAAAAGGGTATCTAGAAGGTGAGGTGATTTT ATG AAA AAG AAT ATC GCA TTT CTT CTT
                       xbaI
                                    1
ala ser met phe val phe ser ile ala thr asn ala thr asn ala tyr ala phe pro thr ile pro leu
GCA TCT ATG TTT GTT TTC TCT ATT GCT ACT ACA AAT GCT ACA AAT GCC TAT GCA TTC CCA ACT ATA CCA CTA
          -10                                                                  20
ser arg leu phe asp asn ala met leu arg ala his arg leu gln leu ala phe asp
TCT CGT CTA TTC GAT AAC GCT ATG CTT CGT GCT CAT CGT CTT CAT CAG CTG GCC TTT GAC
                10                                                40
thr tyr gln phe glu glu ala tyr ile pro lys glu gln lys tyr ser phe leu gln
ACC TAC CAG GAG TTT GAA GAA GCC TAT ATC CCA AAG GAA CAG AAG TAT TCA TTC CTG CAG
                30
```

Fig. 5.

```
                    50                      60                      70
asn pro gln thr ser leu cys phe ser glu ser ile pro ser asn arg glu glu thr gln gln lys ser asn
AAC CCC CAG ACC TCC CTC TGT TTC TCA GAG TCT ATT CCG TCC AAC AGG GAG GAA ACA CAA CAG AAA TCC AAC 80                      90                     100
leu glu leu arg ile ser leu leu ile gln ser trp leu glu pro val gln phe leu arg ser val phe ala asn
CTA GAG CTG CGC ATC TCC CTG CTG ATC CAG TCG TGG CTG GAG CCC GTG CAG TTC CTC AGG AGT GTC TTC GCC AAC 110                     120                     130
ser leu val tyr gly ala ser asp ser asn val tyr asp leu lys lys asp leu glu glu gly ile gln thr leu
AGC CTA GTG TAC GGC GCC TCT GAC AGC AAC GTC TAT GAC CTC CTA AAG AAG GAC CTC GAG GAA GGG ATC CAA ACG 140                     150                     160
met gly arg leu glu asp gly ser pro arg thr gly gln ile phe lys gln thr tyr ser lys phe asp thr asn
CTG ATG GGG AGG CTG GAA GAT GGC AGC CCC CGG ACT GGG CAG ATC TTC AAG CAG ACC TAC AGC AAG TTC GAC ACA 170                     180                     190 191
ser his asn asp asp ala leu leu lys asn tyr gly leu leu tyr cys phe arg lys asp met asp lys val glu
TCA CAC AAC GAT GAC GCA CTA CTC AAG AAC TAC GGG CTG CTC TAC TGC TTC AGG AAG GAC ATG GAC AAG GTC GAG thr phe leu arg ile val gln cys arg ser val glu         gly ser cys phe AM                                    rpBR322
ACA TTC CTG CGC ATC GTG CAG TGC CGC TCT GTG GAG         GGC AGC TGT TTC TAG CTGCCCTTAATGCGGTAGTTTATCACAGTT
                                                                          SmaI-Blunt HindIII junction
```

*Fig.5(Cont.)*

```
GAATTCAACTTCTCCATACTTTGGATAAGGAAATACAGACATGAAAAATCTCATTGCTGAGTTGTTATTTAAGCTTGCC

CAAAAAGAAGAAGAGTCGAAAGAACTGTGTGCGCAGGTAGAAGCTTTGGAGATTATCGTCACTGCAATGCTTCGCAATA

TGGCGCAAAATGACCAACAGCGGTTGATTGATCAGGTAGAGGGGGCGCTGTACGAGGTAAAGCCCGATGCCAGCATTCC

TGACGACGATACGGAGCTGCTGCCGATTACGTAAAGAAGTTATTGAAGCATCCTCGTCAGTAAAAGTTAATCTTTTC
                                                              AP -      SD
AACAGCTGTCATAAAGTTGTCACGGCCGAGACTTATAGTCGCTTGTTTTGTTTTTATTTTTAATGTATTGTACATGGAGAA
        -21 -20                                   -10
        met lys gln ser thr ile ala leu ala leu leu pro leu leu phe thr pro val
AATAAA  GTG AAA CAA AGC ACT ATT GCA CTG GCT CTC TTA CCG CTC TTA CTG TTT ACC CCT GTG
                1                                10
thr lys ala phe pro thr ile pro leu ser arg leu phe asp asn ala met leu arg ala
ACA AAA GCC TTC CCA ACT ATA CCA CTA TCT CGT CTA TTC GAT AAC GCT ATG CTT CGT GCT
                20                               30
his arg leu his gln leu ala phe asp thr tyr gln phe glu glu ala tyr ile pro
CAT CGT CTT CAT CAG CTG GCC TTT GAC ACC TAC CAG GAG TTT GAA GAA GCC TAT ATC CCA
                40                               50
lys glu gln lys tyr ser phe leu gln asn pro gln thr ser leu cys phe ser glu ser
AAG GAA CAG AAG TAT TCA TTC CTG CAG AAC CCC CAG ACC TCC CTC TGT TTC TCA GAG TCT
```

Fig.6.

```
                                60                                    70
ile pro thr pro ser asn arg glu thr gln gln lys ser asn leu glu leu leu arg
ATT CCG ACA CCC TCC AAC AGG GAG ACA CAA CAG AAA TCC AAC CTA GAG CTG CTC CGC 80                                    90
ile ser leu leu leu ile gln ser trp leu glu pro val gln phe leu arg ser val phe
ATC TCC CTG CTG CTC ATC CAG TCG TGG CTG GAG CCC GTG CAG TTC CTC AGG AGT GTC TTC 100                                   110
ala asn ser leu val tyr gly ala ser asp ser asn val tyr asp leu leu lys asp leu
GCC AAC AGC CTA GTG TAC GGC GCC TCT GAC AGC AAC GTC TAT GAC CTC CTA AAG GAC CTA 120                                   130
glu glu gly ile gln thr leu met gly arg leu glu asp gly ser pro arg thr gly gln
GAG GAA GGC ATC CAA ACG CTG ATG GGG AGG CTG GAA GAT GGC AGC CCC CGG ACT GGG CAG 140                                   150
ile phe lys gln thr tyr ser lys phe asp thr asn ser his asn asp asp ala leu leu
ATC TTC AAG CAG ACC TAC AGC AAG TTC GAC ACA AAC TCA CAC AAC GAT GAC GCA CTA CTC 160                                   170
lys asn tyr gly leu leu tyr cys phe arg lys asp lys val glu thr phe leu
AAG AAC TAC GGG CTG CTC TAC TGC TTC AGG AAG GAC AAG GTC GAG ACA TTC CTG 180                            190 191
arg ile val gln cys arg ser val glu gly ser cys gly phe AM
CGC ATC GTG CAG TGC CGC TCT GTG GAG GGC AGC TGT GGC TTC TAG CTGCCC
```

*Fig.6(Cont.)*

PERIPLASMIC PROTEIN RECOVERY

Reference is made to related copending U.S. Ser. No. 658,342 and U.S.S.N. 658,095, both filed of even date.

This application relates to methods for manufacturing proteins in bacteria. It particularly is concerned with isolating eukaryotic proteins from the periplasm of transformed bacteria while minimizing proteolytic degradation of the protein and contamination by nonperiplasmic proteins.

Literature that should be consulted in regard to this application is U.S. Pat. Nos. 4,375,514 and 4,411,994; U.K. patent application No. 2,091,268A (published 1982); I. Palva et al., "Gene" 22: 229-235 (1983); H. Inouye et al., "J. Bact" 148(2): 434-439 (1983): K Talmadge et al., "P.N.A.S. USA" 77(7): 3988-3992 (1980); K. Talmadge et al., "P.N.A.S. USA" 77(6): 3369-3373 (1980); European Patent application No. 114,695; R. Picken et al., "Infection and Immunity" 42(1): 269-275 (1983); T. Silhavy et al., "Microbiological Reviews" 47(3): 313-344 (Sept. 1983); J. Kadonaga et al., "J. Biol. Chem." 259(4): 2149-2154 (Feb. 1984); International PCT application WO 84/00774 (Mar. 1984); O. Zemel-Dreasen et al "Gene" 27. 315 322 (1984); S. Michaelis et al., "J. Bact." 154(1): 366-374 (Apr. 1983); European Patent application No. 114,695 (published Aug. 1, 1984); G. Gray et al., "Biotechnology" pp 161-165 (Feb. 1984); H. Neu et al., "J. Biol. Chem." 240 (9): 3685-3692 (1965); P. Calcott et al., "Can. J. Microbiol." 30: 339-344 (1984); and R. MacLeod et al., Symp. Soc. Gen. Microbiol. 26: 81-109 (1976).

Many naturally occurring secretory and membrane proteins are initially synthesized as intracellular preproteins. These are proteins in which a "signal" polypeptide is linked to the amino acid residue that will become the amino terminus of the mature protein upon secretion. The signal polypeptide is a peptide sequence which enables the mature protein to pass through a cellular membrane. The signal peptide is cleaved away, or "processed", in passing through the cellular membrane by a mechanism that is under study. If the processing occurs properly the mature protein will be free of any amino terminal extraneous signal amino acid residues and will have the proper amino terminal amino acid. Thus, if a homologous or heterologous gene which includes the DNA encoding a signal sequence is expressed by a host gram negative bacterial cell and the signal is then cleaved properly by the host, the mature protein without an appended methionine moiety is secreted into the periplasmic space of the host, i.e., the space between the inner, or cytoplasmic, membrane and the outer membrane of the host. Also known are host-vector systems in which the signal protein and at least an amino terminal portion of the mature protein ordinarily associated with the signal is expressed and processed while linked to a heterologous protein, thereby resulting in the secretion of a fusion protein.

Secretion of mature eukaryotic protein into the periplasm of gram negative bacteria such as *E. coli* has been an objective of the art for a number of years. Periplasmic secretion is a desirable objective because the product is thereby compartmentalized between the inner and outer cell membranes of the culture cells and not exposed to the rigors of the extracellular medium. Exposure to these rigors, e.g., dilution, unfavorable salts or pH, oxidation, foaming, mechanical shearing and proteases, has handicapped the commercialization of nonperiplasmic secretion systems such as those using bacillus or yeast. Also, periplasmic compartmentalization simplifies recovery and purification of the desired mature eukaryotic protein.

Synthesis of animal growth hormone in bacterial hosts is of particular interest. Animal growth hormone is a normal product of the pituitary gland. Animal growth hormones are now known to exhibit a degree of species cross-specificity, a function of similar amino acid sequence and conformation. Human growth hormone (hGH) consists of 191 amino acids and has a molecular weight of about 21,500. HGH is in clinical use for the treatment of hypopituitary dwarfism. It also has been proposed to be effective in the treatment of burns, wound healing, dystrophy, bone knitting, diffuse gastric bleeding and pseudoarthrosis.

It is now known that gram negative organisms are able to synthesize and process to the periplasm modest quantities of eukaryotic protein by recognizing partial or complete eukaryotic signals. In this connection, copending U.S. Pat. No. 488,232, filed Apr. 25, 1983 provides for the synthesis and secretion of mature hGH in prokaryotic hosts by transforming such hosts with prehGH, i.e., with hGH having its normal eukaryotic signal sequence. Host cells were able to express prehGH, to recognize the eukaryotic signal and to process the preprotein properly. Mature hGH was then recovered from the cells.

Mature eukaryotic proteins also are secreted into the periplasm by transformation of host cells with DNA encoding direct hybrid fusions of prokaryotic signals with mature eukaryotic proteins. See copending U.S.Ser. No. 658,342, filed of even date.

One currently used technique for recovery of periplasmic protein is called spheroplasting (H. Neu et al., 1964, "Biochem. Biophys. Res. Comm." 17: 215). This process entails the use of lysozyme to lyse the bacterial wall. It is not attractive particularly for large scale recovery of therapeutic proteins because it entails the addition of another contaminant protein to the periplasmic extract and the spheroplasts are mechanically and osmotically fragile. Further, lysozyme is relatively costly.

Another method is called osmotic shock (H. Neu et al., 1965, "J. Biol. Chem." 240(9): 3685-3692). This is disadvantageous principally because it requires two steps, first treatment of viable cells with a solution of high tonicity and second with a cold water wash of low tonicity to release the periplasmic proteins.

These methods have been practiced on viable cells. The use of viable cells is undesirable because their proteolytic enzymes are fully active. When applicants attempted to recover secreted hGH from a viable culture of *E. coli*, a proteolytic clip of unknown origin removed the amino terminal phenylalanine from about 10 to 20 percent of the hGH.

Accordingly, it is an objective herein to provide improved methods to recover periplasmic proteins. Such improved methods would minimize proteolytic degradation by proteases during recovery, and in general would be sufficiently delicate to minimize contamination of periplasmic protein by intracellular proteins. They also would permit the recovery of large proportions of periplasmic protein by manipulative steps more amenable to commercial, large scale use than currently available procedures, and would not entail the use of contaminating proteinaceous reagents.

SUMMARY

The method herein generally comprises obtaining viable or killed cells which have been transformed to secrete a heterologous or eukaryotic protein, causing the outer membrane of the cells to become permeable for passage of the protein out through the membrane as for example by freezing and thawing, and separating the periplasmic proteins, including secreted eukaryotic protein, from the remainder of the cells. It also is advantageous to culture the cell under phosphate-limiting conditions to engender changes in the cell membranes which enhance recovery of the periplasmic protein.

A novel killing method is provided wherein transformed cells are contacted with an alkanol and heated. These cells then are treated by a cold shock method comprising freezing and thawing which enables recovery of periplasmic proteins.

These methods are employed to particular advantage in recovering hGH from gram negative organisms which express and process a direct hybrid fusion of the E. coli STII enterotoxin signal with mature hGH.

BRIEF DESCRIPTION OF THE DRAWINGS

FIG. 1 discloses the STII gene, including its translated and untranslated regions. The principal portion of its S.D. sequence is overlined at nucleotides 155-161. The imputed amino acid sequence for the STII signal is located at residues −23 to −1 and for the mature STII enterotoxin at residues 1-48. FIG. 1 also discloses the processing site for STII (designated "cleavage site") and various restriction enzyme sites. The asterisk designates the likely mRNA synthesis initiation site assuming that the STII promoter includes the overlined structures at position 84 to 90 and 108 to 115.

FIGS. 2a-2d disclose the construction of a vector (ptrp-STII-hGH) encoding a secretable STII-hGH fusion protein under the control of the trp promoter and containing an STII S.D. sequence.

FIG. 3a is a detail of the nucleotide sequence in the vicinity of the hGH gene in ptrp-STII-hGH.

FIG. 5 is a detail of the nucleotide sequence in the vicinity of the hGH gene in pAP-STII-hGH.

FIG. 6 is the nucleotide sequence of the AP promoter region, the AP signal and the hGH gene in pAP-1.

DETAILED DESCRIPTION

Figure 2A:
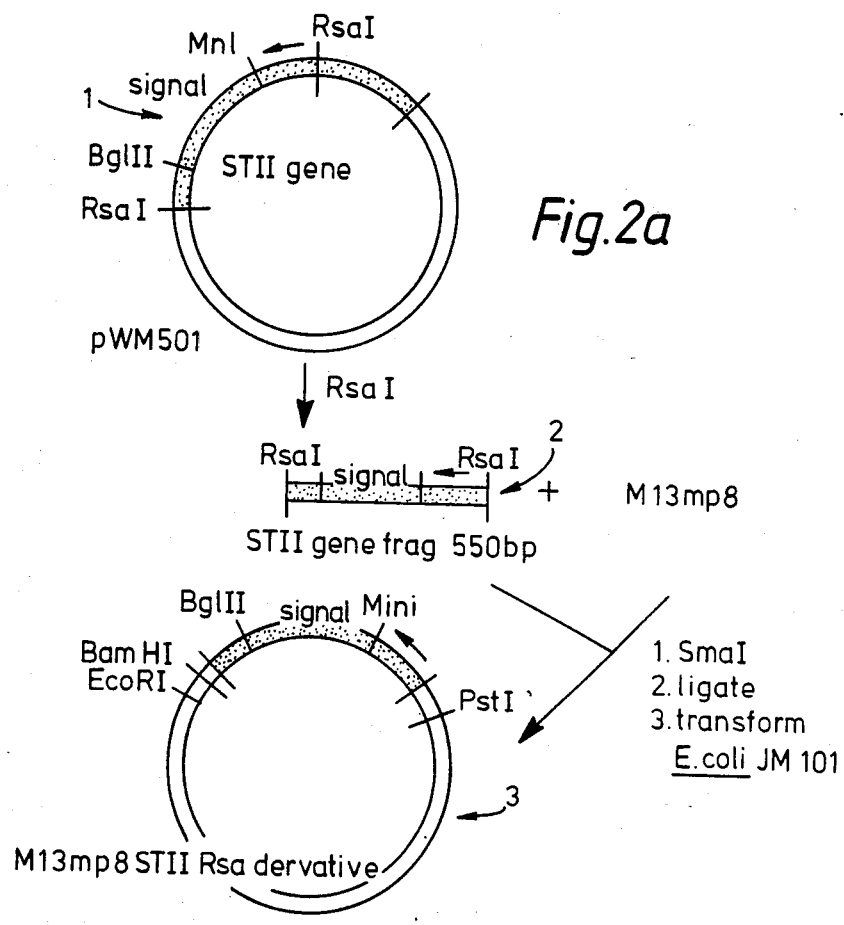
Figure 2A:
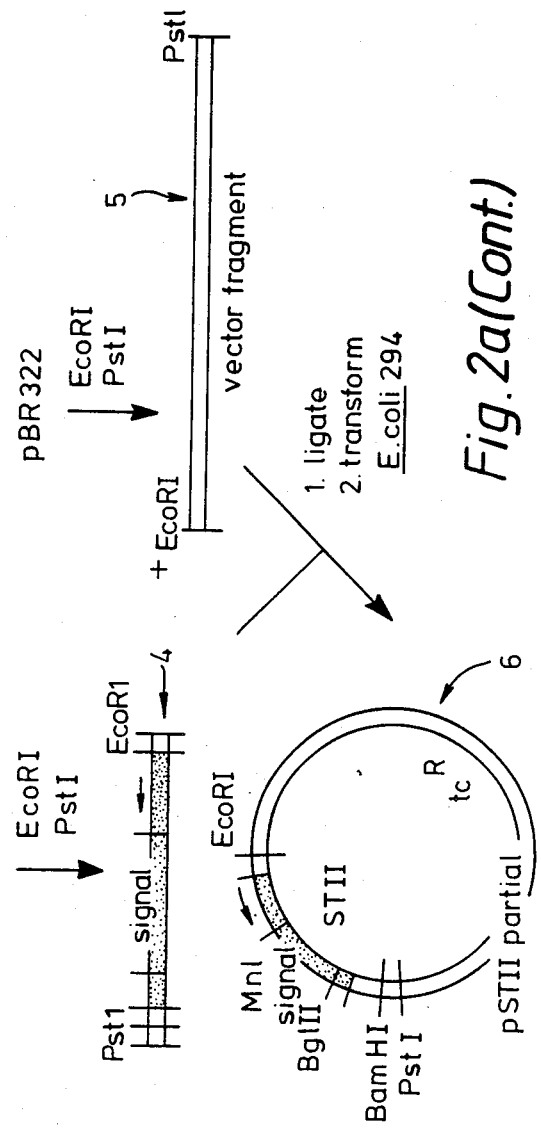

The bacterial cells to be treated herein are organisms having a periplasmic space. These generally are gram negative organisms, and do not include bacteria such as bacillus species or eukaryotic cells. Gram negative organisms such as E. coli which are transformed to express and secrete a heterologous protein are preferred.

A heterologous protein is a protein not ordinarily secreted by the bacterial cell. While such a protein may be an ordinarily intracellular protein of the transformed cell that has been engineered for secretion, or it may be a protein encoded by DNA from another microbe, ordinarily it is a eukaryotic protein, a fragment thereof or a fusion thereof with a prokaryotic protein or fragment. Preferably the periplasmic protein is a mature eukaryotic protein such as a hormone, e.g., hGH, an interferon or a lymphokine.

The cells to be treated herein may be obtained from cultures of transformed bacteria grown in conventional media or media tailored to the vectors or mutant host transformants used to secrete the heterologous protein.

In the preferred embodiment the cells are be grown under phosphate limiting conditions prior to harvest of the culture. This is the case whether or not the organism is transformed with a vector encoding a eukaryotic protein under the control of a promoter for a phosphate processing protein, or whether the cell is defective in transporting or catabolizing phosphate nutrients. Surprisingly, the use of a phosphate-limiting culture medium prior to cell harvest during the late stages of fermentation greatly improves the mechanical characteristics of transformed gram negative organisms. These characteristics enhance the efficacy of the cold shock extraction method described infra. The medium is made phosphate limiting, for example, by either precipitating the phosphate from the medium, by introducing phosphate to the culture at a limiting feed rate, or by providing an initial supply of phosphate that will be inadequate to support optimal growth of the culture beyond a certain predetermined density. The initial supply will be sufficient to support optimal cell growth during early stages of the fermentation, for example log phase growth or to an $OD_{550}$ of about 45. The amount of phosphate will be tailored to the other nutrients and to the strain of organism used in the culture. Ordinarily, about 2.5 g/l of potassium/sodium phosphate salts are employed in media for use with E. coli W3110 (ATCC 27325), but larger amounts (about 4.0 g/l) are used with cells having phosphate metabolism defects such as the phoT mutant. This is in contrast with nonlimiting quantities of phosphate (about 9.0 g/l). The amount of phosphate ion in the limiting culture medium at the point the culture becomes limiting is less than about 1 mM. Typically the cells are cultured under these limiting conditions for at least about 1 hour prior to harvest.

Preferably the cells are permitted to accumulate periplasmic heterologous protein to a maximum level, usually during a growth stage following logarithmic growth, prior to initiation of the treatment provided herein. The cells should be killed as soon as this point is reached or shortly thereafter. The term "killed" means that the cells at least are unable to replicate. It is likely, however, that treatment with alkanol and heat as is further described infra interdicts or destroys metabolic functions not directly associated with replication. However, other than elimination of a deleterious proteolytic activity of E. coli towards periplasmic hGH the impacted metabolic functions remain unknown. The killing procedure should not rupture, lyse or weaken the inner cell membrane of the host organism.

Cells that have reached the desired point of growth are preferably killed by immediately contacting them with an alkanol and heating. The alkanol should not be an alkanol which is lytic for cell membranes, e.g. 1-octanol. Generally, suitable alkanols include lower ($C_2$ to $C_4$) monohydroxy alkanols such as 1-butanol or ethanol, preferably 1-butanol. The alcohol should be contacted with the cells by adding the alkanol to the fermentation culture while continuously mixing.

The amount of alcohol which is added will be such as to bring the culture to an alkanol concentration of about from 0.5 percent to 10 percent vol/vol, and preferably about to 1.5 percent vol/vol for 1-butanol. Butanol is preferred because as little as about 0.5 percent can be used; larger proportions are needed for equivalent inactivation when using a propanol or ethanol.

Contemporaneous with or after the addition of alkanol to the cell culture, the temperature of the culture is increased to and held at a level sufficient in conjunction with alkanol to kill the cells. Ordinarily this will be about from 0.5 to 20 minutes at a temperature of about from 55° C. to 35° C., the higher temperatures being employed for the lesser periods. The alkanol enables the heating to be conducted at a lower temperature than would otherwise be required, an advantage in preserving the activity of proteins to be recovered.

Cell killing is not critical. Since it is useful in preventing or retarding product degradation it may be dispensed with if the cells can be processed quickly and regulatory requirements for handling recombinant cells can be otherwise complied with. However, we have found that killing the cells approximately doubles the product protein recovery without reducing the purity of the product protein in the recovered supernatants.

After the cells are cultured and/or killed, periplasmic protein is recovered. This generally entails forming a paste of the cells, freezing the cells, thawing the cells, suspending them in buffer, and separating the periplasmic proteins from cell debris, e.g. by low speed centrifugation or filtration. The periplasmic proteins, including secreted eukaryotic proteins, are located in the supernatant. Eukaryotic periplasmic proteins may be obtained in higher specific activity, i.e. purity, than is attained with osmotic shock methods, and treatment with a hypertonic agent such as 20 percent sucrose is not required, but it should be understood that any method for causing the outer membrane of the cell to become permeable to the periplasmic protein can be used with killed cells.

The cell paste to be frozen is produced by centrifuging or filtering the cell culture and recovering the cell mass. This paste typically contains residual quantities of the fermented culture medium, e.g. LB (Luria Broth) medium; it is unnecessary to wash the cells with a freezing menstruum prior to the subsequent steps. It is not critical that a cell paste be formed as the cold shock extraction method herein is largely independent of cell density. However, the economics of freezing and thawing large volumes of material are such that small paste volumes are preferred.

The cell freezing should be as soon as possible. Generally the paste at room temperature is placed in a freezer at −20° C. until frozen, and then stored at −80° C. until further processing is required.

The frozen paste is thawed and diluted into several volumes of water or aqueous buffer, preferably about 3 or greater volumes of 10 mM tris-HCl buffer at pH8. This buffer is hypotonic to the intracellular contents of the host organisms. The following steps are performed at about 4° C. The dilutions generally should be about 3 volumes of buffer, although the identity, concentration, and pH of buffer will vary depending upon the periplasmic protein to be recovered.

The cells are thoroughly suspended in the buffer. This step is facilitated by suspending the cells in the buffer by use of a homogenizer set at a speed at which no substantial lysis of the cells occurs.

The suspended cells are gently stirred for about from 10 to 60 minutes, ordinarily about 30 minutes. Then the cell debris and cells (containing cytoplasmic proteins) are removed by centrifugation, typically 12,000× g for 30 minutes, or by filtration. The supernatant contains the periplasmic proteins, solubilized outer membrane proteins, residual culture medium and extracellular proteins, and a small proportion of soluble intracellular proteins. The desired eukaryotic protein may be purified from the supernatant in accord with further procedures as desired.

The freeze-thaw extraction method described above offers considerable advantages in terms of yield and, surprisingly, purity of the desired periplasmic protein when compared to extraction of either fresh killed or unkilled transformants with buffer alone. Approximately 5 to 26 times as much hGH is recovered from frozen unkilled cells than from unfrozen, unkilled buffer-extracted cells. The supernatants from frozen killed cells were about 19 percent hGH by weight of total protein, but from fresh killed cells only about 16 percent hGH.

The foregoing method is applied in the following Examples to the recovery of hGH from *E. coli* transformed with a vector which expresses mature hGH as a direct hybrid fusion with the *E. coli* heat stable enterotoxin STII signal peptide. However, it will be appreciated that the recovery method herein is applicable to the separation of periplasmic proteins from transformed bacterial cells in general, e.g. those disclosed in U.S. Pat. Nos. 4,411,994 and 4,375,514; K. Talmadge et al., op cit (both citations); 0. Zemel-Dreasen et al., op cit and G. Gray et al., op cit.

In order to simplify the Examples certain frequently occurring and well-known methods employed in recombinant constructions will be referenced by shorthand phrases or designations.

Plasmids are designated by a lower case p preceded and/or followed by capital letters and/or numbers. The starting plasmids or sources of DNA herein are commercially available, are publically available on an unrestricted basis, or can be constructed from available plasmids or polynucleotides in accord with published procedures. In addition, other equivalent plasmids are known in the art and will be apparent to the ordinary artisan since the plasmids generally only function as replication vehicles for the preprotein and its control sequences, or for elements thereof in intermediate constructions.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate.

The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the DNA from the gel, generally by electroelution. This procedure is known generally. For example, see R. Lawn et al., 1981, "Nucleic Acids Res." 9: 6103–6114, and D. Goeddel et al., 1980, "Nucleic Acids Res." 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503–517, and hybridization as described by T. Maniatis et al., 1978, "Cell" 15: 687–701.

"Transformation" means introducing DNA into an organism so that the DNA is replicable, either as an extrachromosomal element or chromosomal integrant. Unless otherwise provided, the method used herein for transformation of *E. coli* is the CaCl$_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All literature citations are expressly incorporated by reference.

EXAMPLE 1

Construction of a Plasmid Encoding for the *E. coli* Heat-Stable Enterotoxin (STII) Gene Signal Peptide Sequence.

The following construction is illustrated in FIG. 2a. The plasmid pWM501 (Picken et al, op cit) contains the heat-stable enterotoxin (STII) gene. A portion of the DNA which encodes the STII gene was recovered from pWM501 1 (stippled region of FIG. 2a) using the following steps. pWM501 was digested with RsaI and the 550 bp DNA fragment 2 was isolated. This gene fragment was ligated to the phage M13mp8 (J. Messing et al. in the *Third Cleveland Symposium on Macromolecules: Recombinant DNA*, Ed. A. Walton, Elsevier, Amsterdam (1981) pp 143–153) that had been previously digested with SmaI. The ligated DNA was used to transform *E. coli* JM101, a commercially available strain for use with the M13 phage. Clear plaques were recovered. The double stranded M13mp8 STII Rsa derivative 3 was isolated from an *E. coli* JM101 infected with this phage using standard procedures (J. Messing et al. op cit). By the use of the M13mp8 subcloning procedure just described the approximately 550 base pair fragment 2 containing the STII leader gene is now bounded by a series of different restriction endonuclease sites provided by the phage. The M13mp8 STII Rsa derivative 3 then was digested with EcoRI and Pst I and a DNA fragment 4 slightly larger than fragment 2 was isolated.

EcoRI-PstI fragment 4 was subcloned into pBR322. This was accomplished by digesting pBR322 with EcoRI and PstI and isolating the vector 5. The isolated vector 5 was ligated to the EcoRI-PstI DNA fragment 4. This DNA mixture was used to transform *E. coli* 294 and tetracycline resistant colonies selected. A plasmid 6 was isolated from a resistant *E. coli* colony and designated pSTII partial.

EXAMPLE 2

Construction of a Plasmid encoding the STII Signal Peptide Under the Control of the Trp Promoter.

Figure 2B:
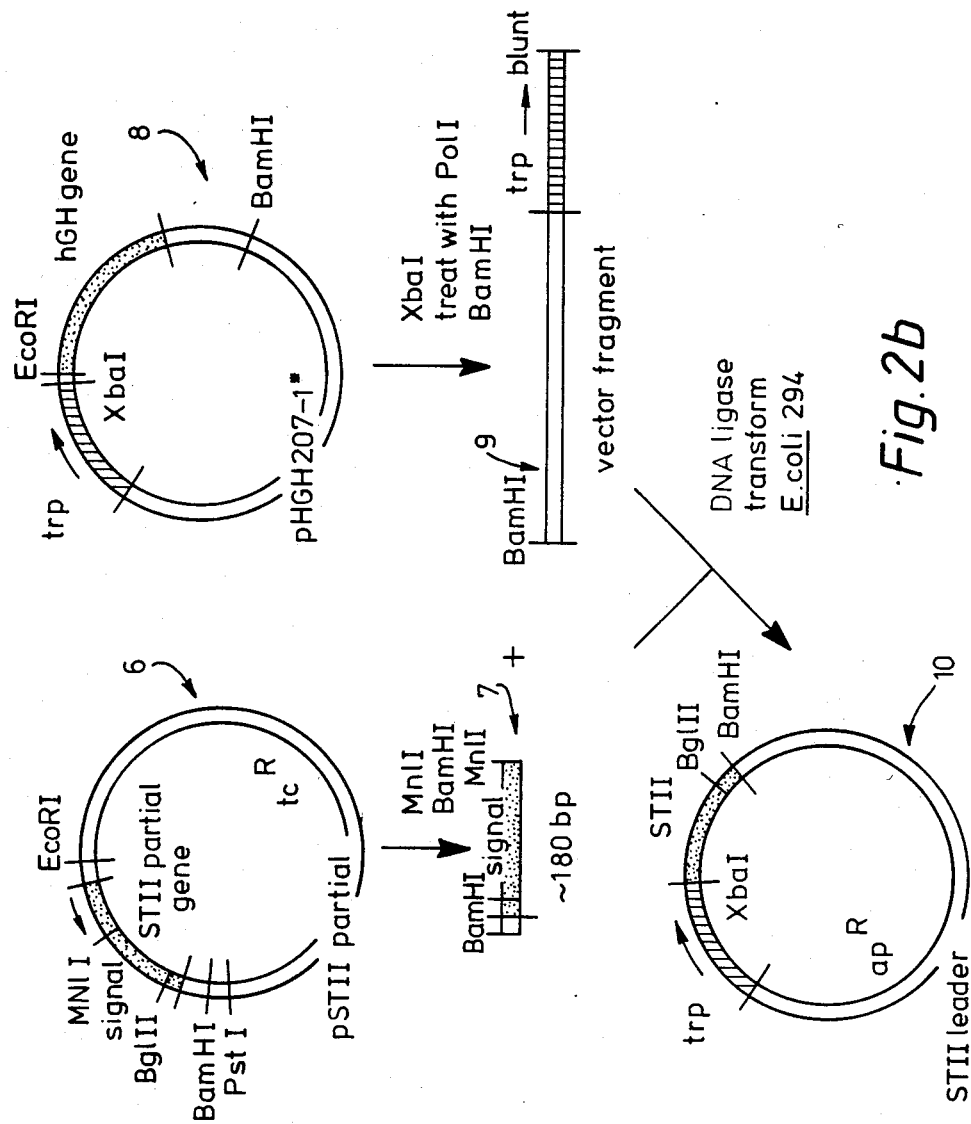

This construction method is shown in FIG. 2b. pSTII partial from Example 1 was digested with MnlI and BamHaI and a 180 bp fragment 7 containing the STII S.D. sequence, the STII signal sequence, and the first 30 codons of the mature STII gene was isolated. DNA fragment 7 was ligated to a plasmid containing the trp promoter. One such plasmid pHGH207-,1 8, has been described previously (H. de Boer et al., 1982, in: *Promoters: Structure and Function*, Eds. R. Rodreguez et al. Chamberlin, Praeger Pub., New York, NY, pp 462–481). A derivative of this plasmid, pHGH207-1*, wherein the EcoRI site 5' to the trp promotor had been converted to EcoRI* by filling in with DNA polymerase I (DNA pol 1) and joining the blunt ends by ligation (S. Cabilly et al., 1984, "Proc. Natl. Acad. Sci. USA" 81: 3273–3277) was used in this example. The trp promoter-containing plasmid was digested with XbaI and treated with DNA pol I and all four dNTPs to fill in the protruding sequence. The DNA preparation was then digested with BamHI and the vector containing fragment 9 isolated. Vector fragment 9 then was ligated to the 180 bp STII signal-containing DNA fragment 7 isolated above. - 26 The ligation mixture was used to transform *E. coli* 294 to ampicillin resistance. A plasmid designated STII leader 10 was isolated from an ampicillin resistant colony. This plasmid contains the STII signal sequence and a portion of the gene encoding mature STII under the control of the trp promoter. In the following example, the DNA sequence encoding mature hGH was operably ligated downstream from the trp - STII signal sequence.

EXAMPLE 3

Construction of an Expression and Secretion Plasmid for hGH

Figure 2C:
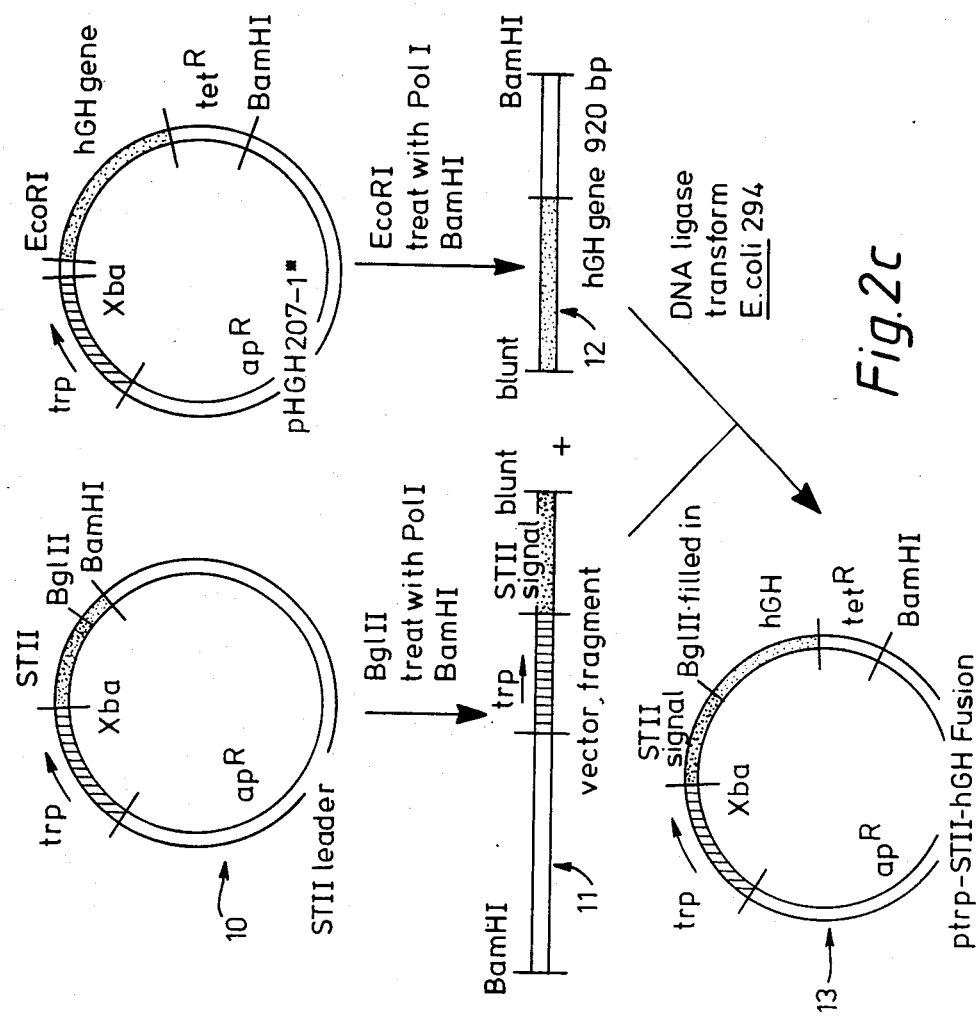

Refer to FIGS. 2c–2d for a schematic display of this method. STII leader 10 was digested with BgIII then treated with DNA pol I and all four NTP's to fill in the protruding end, and then digested with BamHI. The vector-containing fragment 11 was isolated. The plasmid pHGH207-1 from Example 2 was digested with EcoRI, treated with DNA pol I and all four NTP's to fill in the protruding end, and then digested with BaaHI. The hGH ene-containing fragment 12 of about 920 bp was isolated from the BamHI digestion. These two fragments were ligated and the DNA mixture used to transform E. coli 294 to tetracycline resistance. A plasmid designated ptrpSTII-HGH-fusion 13 was isolated from the resistant E. coli colonies. This plasmid still contains extraneous nucleotides encoding a portion of the STII mature protein between the STII leader peptide sequence and the hGH structural gene. These nucleotides were deleted using the M13 site specific mutagenesis procedure (J.P. Adelman et al, 1983, "DNA" 2: 183-193).

Figure 3:
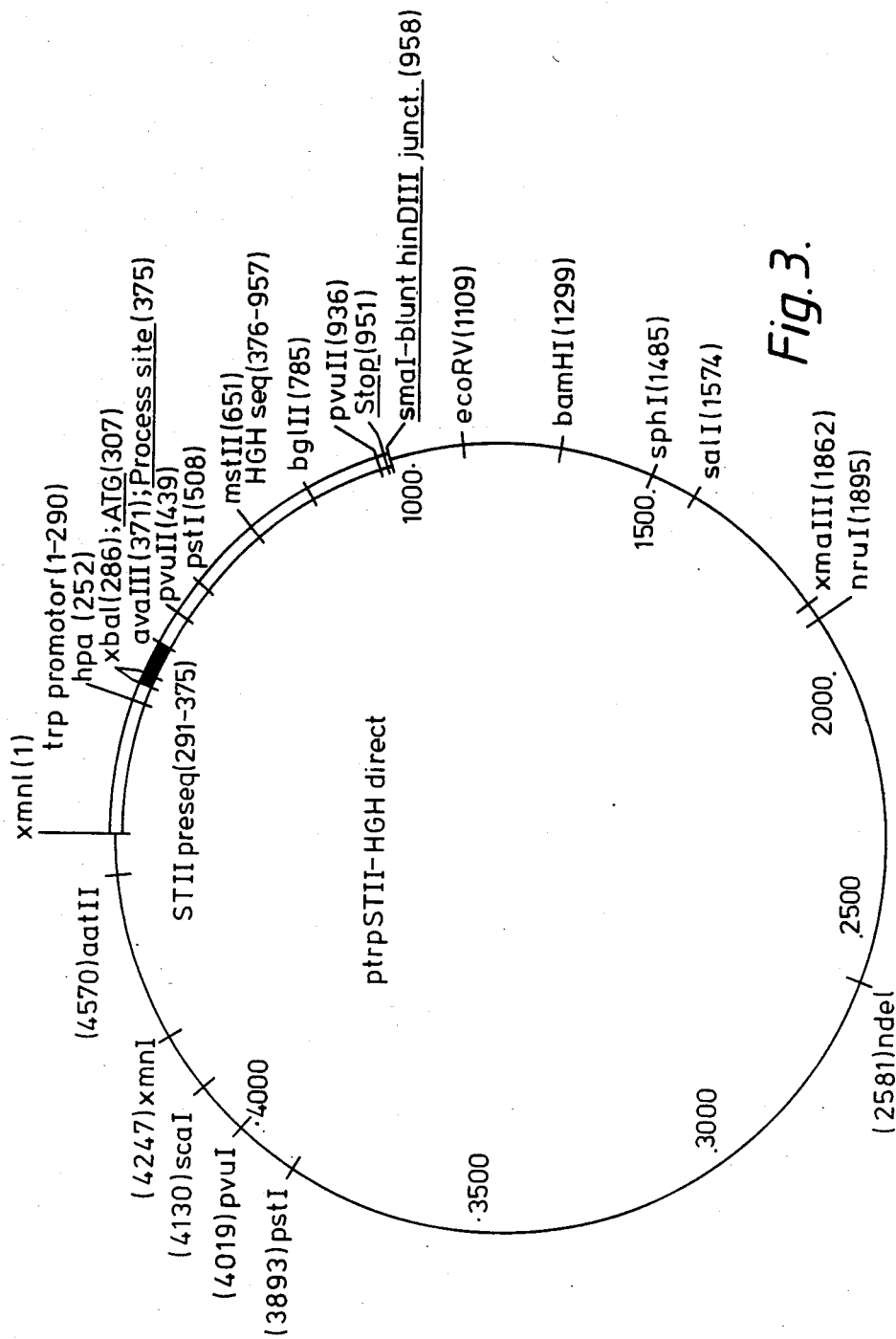
FIG. 3 is a detail of the plasmid trp-STII-hGH.
Figure 3A:
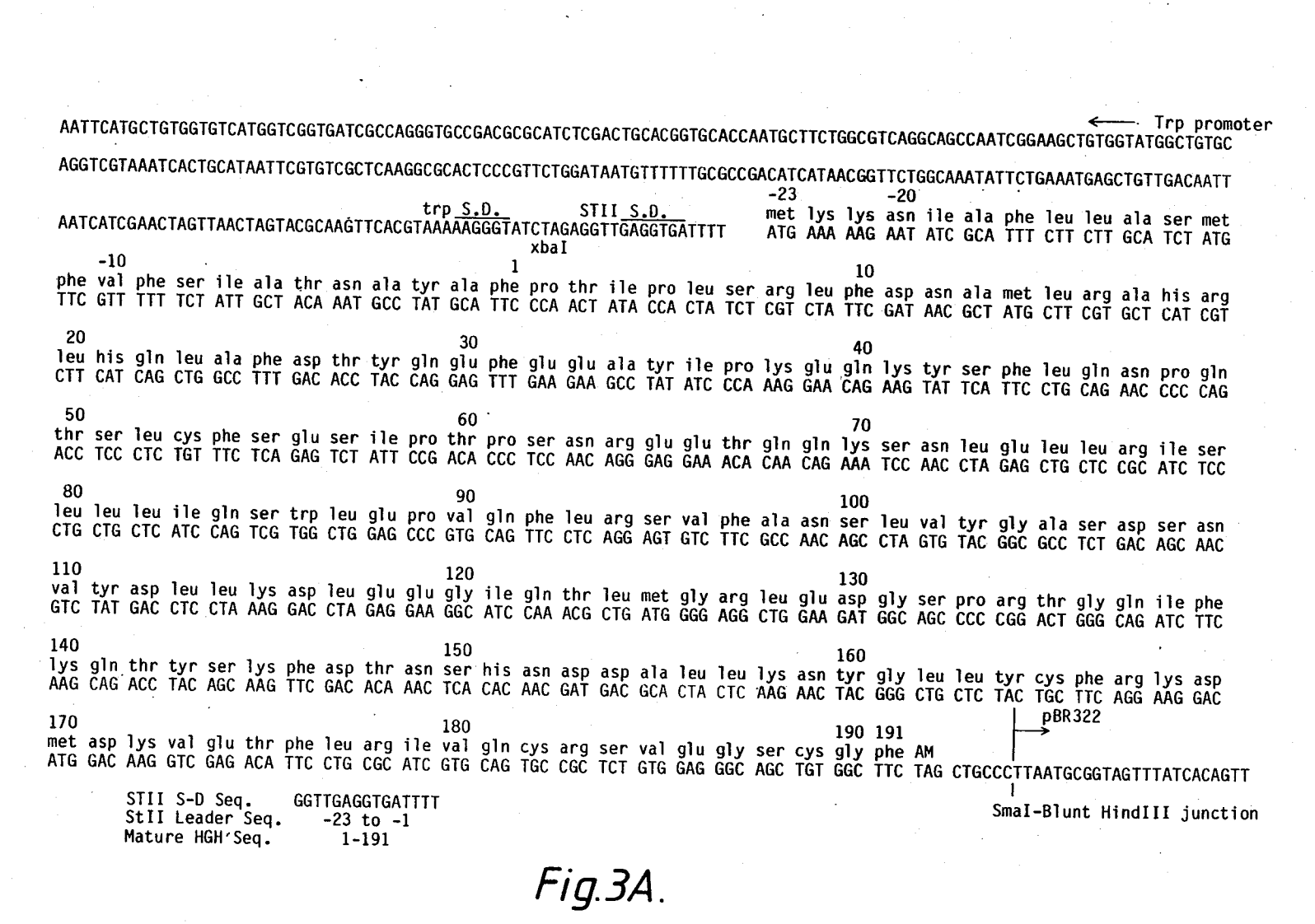

The gene from ptrpSTII HGH fusion 13 was incorporated into the single stranded phage M13mp10 (J. Messing et al., op cit. and J. Adelman et al. op cit.). M13 mutagenesis phage and E. coli strains are commercially available. Mutagenesis was accomplished first by digesting plasmid 13 with XbaI and BamHI and then recovering fragment 14. M13mp10 was digested with XbaI and BamHI and the phage fragment (not shown) was isolated. Fragment 14 was ligated into the phage fragment and the ligation mixtures used to transform JMIOI. The transformed culture was plated and incubated. Phage having the fragment 14 insert were identified as clear rather than blue plaques in the E. coli lawn. Corresponding phage were grown on E. coli JM101, and the culture centrifuged. Single stranded phage 15 are present in the supernatant. Single stranded phage 15 DNA was prepared, annealled to the synthetic oligonucleotide primer 5'pCAAATGCCTATGCATTC-CCAACTATACC-OH3', primer extended with DNA pol I and the four NTPs to obtain double stranded DNA (one of which strands contained the deletion), treated with T4 ligase, extracted and used to transform E. coli JM101 (See J. Adelman et al., op cit). Note that the first 14 nucleotides of the primer are the 5' end of the mature hGH gene, while the last 14 nucleotides are the 3 end of the STII signal. Double stranded phage were obtained from the cellular contents of the transformed JM101, transfected into plated E. coli JM101, transfer filter impressions taken of the plates and double stranded phage containing the deletion were identified on the filters by Southern analysis with a 5'-32P-labelled obigonucleotide having the DNA sequence of the primer. Double stranded DNA 17 was prepared from the E. coli infected with the M13mp10 containing the gene deletion. This DNA was digested with XbaI and BamHI and the DNA fragment 17 isolated. This was ligated in the presence of fragment 18 from similarly digested and isolated pHGH207-1 . The ligation was used to transform E. coli 294 to tetracycline resistance. Plasmid ptrp-STII-HGH 19 was recovered and its nucleotide sequence determined. A detailed restriction map of this plasmid is shown in FIG. 3. The DNA sequence of this plasmid in the vicinity of the hGH gene is shown in FIG. 3a.

EXAMPLE 4

Expression and Secretion of hGH

HGH was synthesized in shake culture using plasmid 19 from Example 3. E. coli 294 was transformed with plasmid 19 and innoculated into 10–20 ml of LB medium with 5 µ/ml tetracycline in a 50 or 125 ml shake flask. The flask was cultured for 12–24 hours at 37° C. without the addition of any further medium, after which the cells were recovered by centrifuging. Total cellular hGH was assayed by radioimmunoassay of sonicated cells. The secreted hGH was recovered through osmotic shock and determined to be mature hGH by SDS-PAGE and amino terminal sequencing. Amounts recovered were about ten times that which is expressed when using the human hGH signal under control of the trp promoter.

EXAMPLE 5

Construction of a Plasmid Designed to Express and Secrete

Human Growth Hormone (hGH) Under the Control of the AP

Promoter and Signal Sequence.

Figure 4A:
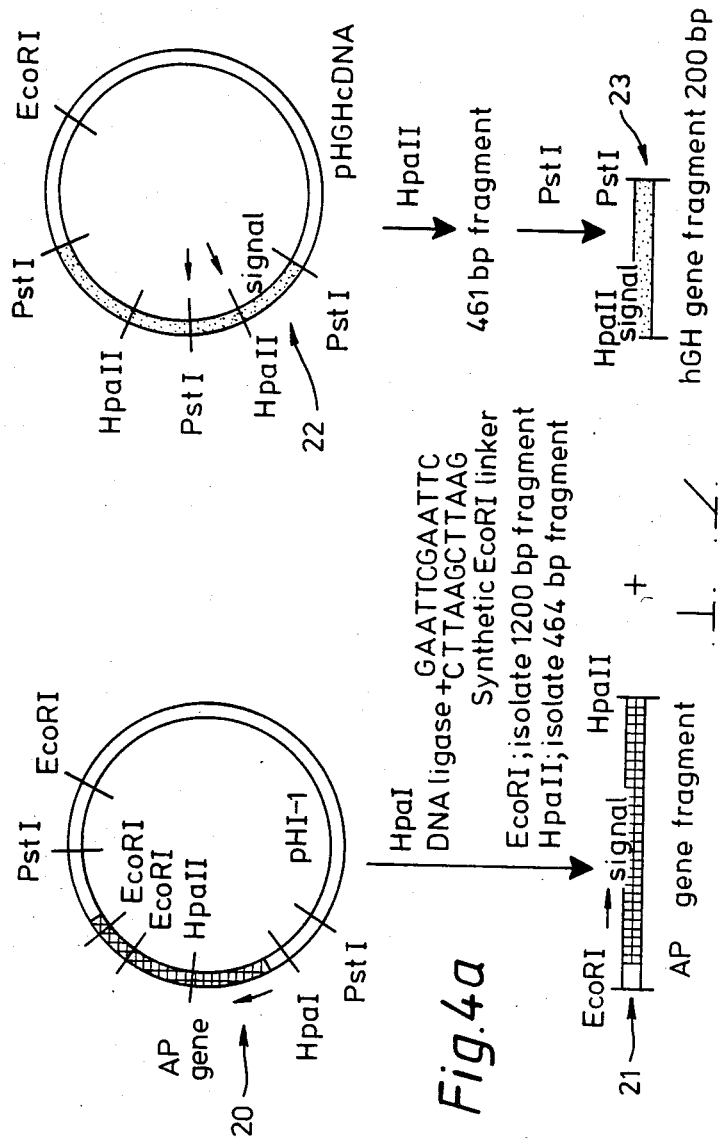
FIGS. 4a-4c disclose the construction of a vector (pAP-STII-hGH) encoding secretable AP-hGH and STII-hGH fusion proteins under the control of the AP promoter, the vector encoding the latter containing an STII S.D. sequence.
Figure 4B:
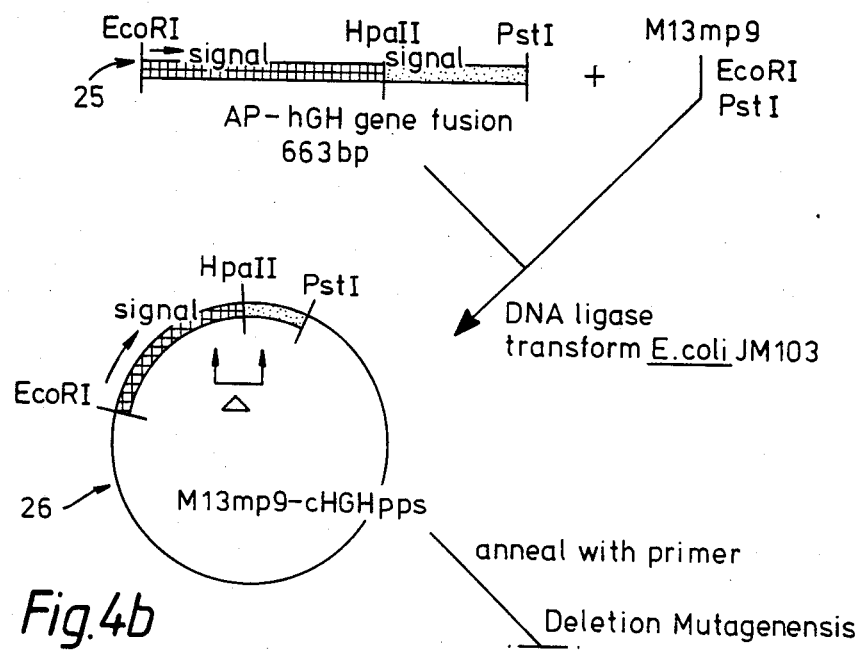
Figure 4C:
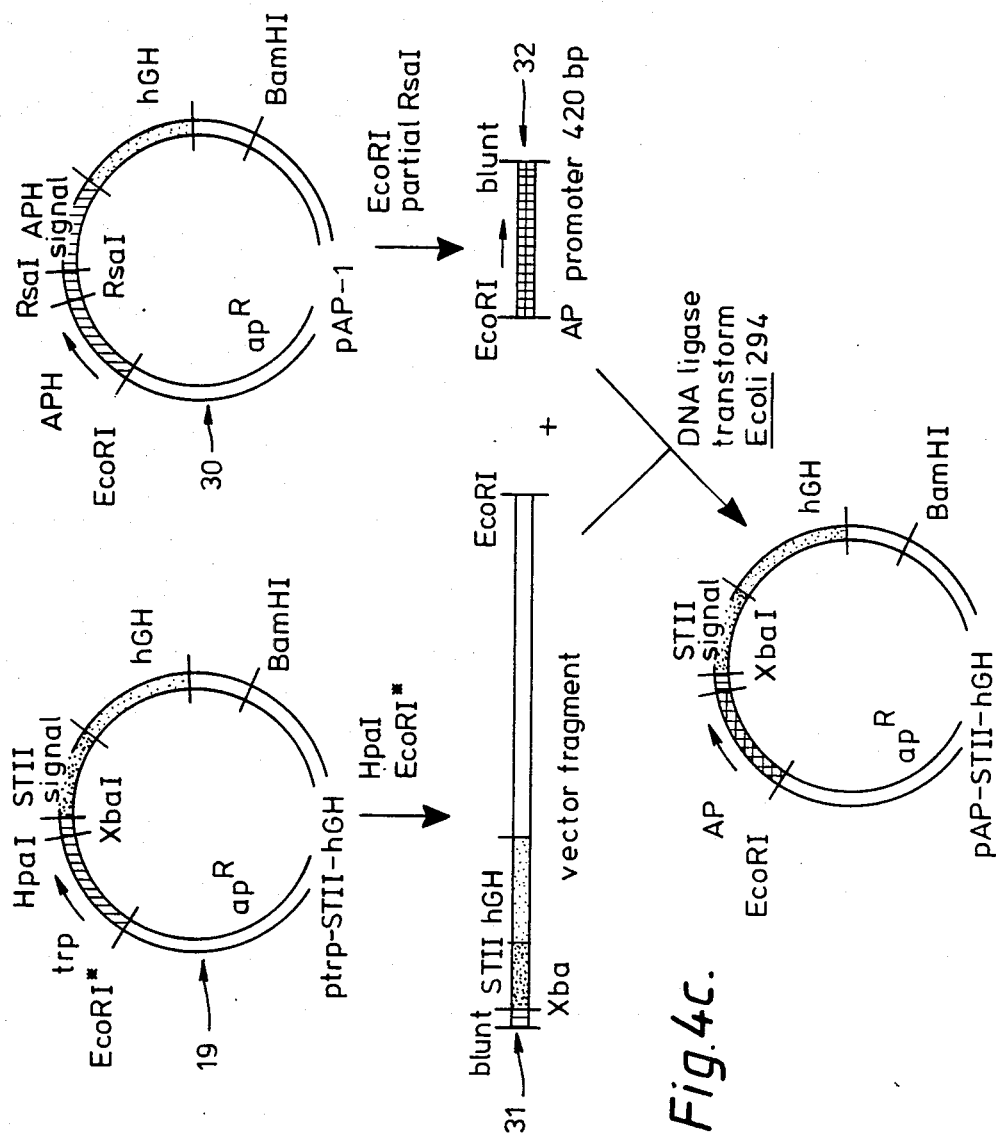

This construction is shown in FIGS. 4a–4c. A DNA fragment containing a portion of the AP gene was isolated from the plasmid pHI-1 20 [Inouye, H., et al., J. Bacteriol. 146: 668–675 (1981)]. This was done using a series of steps to introduce an EcoRI site 5' to the AP gene and promoter sequence. The plasmid 20 was digested with HpaI and then ligated to a linker molecule containing two EcoRI sites in tandem. After heat inactivation of the ligase enzyme the DNA was digested with EcoRI and a 1200 bp fragment isolated. This DNA fragment was then treated with HpaII and a 464 bp fragment 21 isolated. A plasmid 22 containing cDNA prepared from human growth hormone mRNA was prepared as described by Martial et al., "Science" 205: 602–606 (1979) and Roskem et al., "Nucleic Acids Res." 305–320 (1979) (see also European Patent Application No. 84302725.1). Plasmid 22 was digested with HpaII and a 461 bp fragment was isolated. The 461 bp fragment was further digested with PstI and a 200 bp fragment 23 containing part of the hGH gene then isolated. DNA fragments 21 and 23 were ligated to a 3609 bp DNA fragment isolated from pBR322 that had been previously digested with EcoRI and PstI. This DNA ligation mixture was used to transform E. coli 294 to tetracycline resistance. A plasmid 24, designated pcHGHpps, was recovered from a transformant colony.

In plasmid 24 the gene encoding the AP promoter and signal sequence in pcHGHpps was linked to hGH in the same reading frame. However a number of extraneous nucleotides were present between the signal sequence and the beginning of the mature hGH gene. This extraneous nucleotide sequence was deleted by mutagenesis. pcHGHpps was digested with EcoRI and PstI and the 663 bp fragment 25 isolated. Fragment 25 was introduced into MI3mp9 previously digested with PstI and EcoRI. This was ligated and used to transform E. coli JM101. Clear plaques were selected and a derivative phage 26, M13mp9-cHGHpps, was identified and isolated. Phage 26 was annealled to the synthetic oligonucleotide primer 5'PCTGTGACAAAAGCCTTC-CCAACCATTCC-OH3'. The first 14 nucleotides correspond to the sequence of the 3' end of the AP signal peptide and the last 14 correspond to the 5' end of the mature hGH coding sequence. The site-specific deletion mutagenesis was performed as previously described in Example 3 (see also J. Adelman et al. opcit.).

Plaques containing the desired deletion were detected by Southern analysis with the 5'-32P-labeled oligonucleotide primer of this Example. Without enrichment for the desired genotype, nine percent of the plaques screened hybridized to the labelled primer. One of the positives, MI3mp9-AP-1, 27, was determined by the dideoxy chain termination nucleotide sequencing method to have the expected sequence. The partial hGH gene, now correctly fused to the AP promoter and signal gene, was introduced into pHGH207, 28 (H. de TM - Boer et al., op cit). This was accomplished by digesting pHGH207 with PstI and NdeI, and then isolating the 2750 bp fragment. Another sample of pHGH207 was digested with NdeI and EcoRI and a 2064 bp fragment isolated. The M13mp9-AP-1 phage was digested by EcoRI and PstI, and the 602 bp AP hGH partial gene 29 was isolated. The 2750 and 2064 bp fragments were ligated in a three-part ligation with fragment 29, and the ligation mixture then used to transform E. coli 294 to ampicillin resistance. pAP-1 was isolated from a resistant colony and characterized by restriction enzyme mapping and nucleotide sequence analysis.

EXAMPLE 6

Construction of a Plasmid (pAP-STII-hGH) to Express and Secrete hGH Under the Control of the AP Promoter ptrp-STII-hGH (from Example 3) was digested with HpaI and EcoRI and the vector fragment 31 isolated. A 420 bp AP promoter fragment 32 was isolated from the plasmid pAP-1after digestion with EcoRI and partial digestion with RsaI. Fragments 31 and 32 were ligated and used to transform E. coli 294 to ampicillin resistance. The plasmid pAP-STII-hGH was isolated and characterized by restriction enzyme mapping and nucleotide sequence analysis. The nucleotide sequence and translated amino acid sequence of the AP-STII-hGH construction is shown in FIG. 5.

EXAMPLE 7

Recovery of hGH from E. coli Containing the Plasmid pAP-STII-hGH.

E. coli W3110 and 294 were transformed respectively with pAP-STII-hGH or pAP-1 and cultured as described in Example 4 except that the medium used was phosphate depleted. The amounts synthesized and the distribution of processed and unprocessed hGH were determined as described in Example 4. In small volumes ptrp-STII-hGH produces better results, but in 10 liter culture volumes the preferred embodiment is the plasmid pAP-STII-hGH since AP promoted cells can grow to higher densities than trp promoted organisms.

EXAMPLE 8

Large Volume Fermentation and hGH Recovery

Eight hours prior to the start of a 10 liter fermentation a 500 ml inoculum culture is grown up. A transformant of E. coli W3110 tonA, phoA, phoT containing pAP-STII-hGH is inoculated into a sterile 2 liter flask containing 500 ml of LB medium and O tetracycline (0.5 µg/ml). The culture is incubated in a rotary shaker at 37° C. for eight hours. A sterile 10 liter fermentation medium is prepared, containing the following ingredients: 26 g $K_2HPO_4$, 13 g $NaH_2PO_4 \cdot 2H_2O$, 15 g KCl, 50 g $(NH_4)_2SO_4$, 10 g $Na_3$ citrate, 50 ml of 50 percent glucose, 1000 ml of 10 percent NZ-amine YT, 100 ml of IM $MgSO_4$, 5 ml of 2.7 percent $FeCl_3$, 5 ml of trace metals, 1 ml of 5 mg/ml tetracycline, 5 ml of antifoaming agent, and 6.5 liters of $H_2O$. The starting pH of the medium is titrated to 7.5 by adding $H_2SO_4$, and the run is begun by seeding the 500 ml inoculum culture into the 10 liter fermenter. Throughout the run the temperature is maintained at 37° C. and the culture agitated at 650 rpm under aeration. From the outset, the cells are fed glucose (50 percent) at a flow rate of 0.5 ml/min. When the OD 550 is in the range 10–25 the glucose feed rate is manually adjusted to keep the pH at 7.5 and the residual glucose level $\leq$ about ¼ percent. When the OD 550 reaches 25, the glucose feed rate is manually adjusted to drive the $dO_2$ level to 30 percent and thereafter, the glucose feed rate is periodically adjusted to maintain the $dO_2$ level at 30 percent. Thirty-six hours after the start of fermentation the cells are killed and harvested.

The glucose feed and aeration are turned off but the agitation rate of 650 rpm is maintained. 1-butanol is added immediately to the fermenter to yield a final concentration of 1.5 percent vol/vol and steam is immediately injected into the fermenter jacket so that the temperature in the tank rises rapidly to 50° C. When the temperature reaches 50° C., it is held at this temperature for 10 Minutes. Then the fermenter is rapidly cooled below 20° C. and the cellular contents of the fermenter are harvested by centrifugation. The cell paste is first frozen at −20° C. and then transferred to a −80° C. freezer.

The cell paste, frozen at −80° C., is thawed overnight at 4° C. and all subsequent steps are performed at 4° C. The paste is mixed in 4 volumes of 10 mM Tris-HClpH=8.0 and suspended in an Ultra-Turrex homogenizer for 30 seconds to 5 minutes. The suspension is stirred for 30 minutes, with adjustment to pH 8.0 as required, and then the cell debris and cells containing cytoplasmic proteins are removed by centrifugation at 12,000× g for 30 minutes. The periplasmic fraction contains mature hGH at between 0.5 and 1 gram/-liter/100 $OD_{550}$ with about 95 percent of the total of preprotein and mature hGH (as estimated from stained gels) present in the periplasm. About 50–60 percent of the total cellular hGH is recovered in the supernatant. The supernatant contains about 20 percent hGH by weight of protein.

We claim:

1. A method for recovering protein from the periplasmic space of a bacterial cell transformed to secrete a eukaryotic protein, comprising
   (a) contacting the cell with an effective amount of a lower alkanol having between two to four carbon atoms for a time and at a temperature sufficient to kill the cell without lysing the inner membrane;
   (b) freezing the cell;
   (c) thawing the cell; and
   (d) receiving the periplasmic proteins, including the eukaryotic protein, from the remainder of the cell.

2. The method of claim 1 wherein the alkanol is ethanol or butanol.

3. The method of claim 1 wherein the cell is heated for about from 35° C. to 55° C. for about from 0.5 to 20 minutes.

4. The method of claim 1 wherein the contacting and heating are conducted while the cell is in aqueous suspension in culture medium.

5. The method of claim 1 wherein the alkanol is mixed with an aqueous suspension of the cell until an alkanol concentration of about from 0.5 to 10 percent by volume is reached.

6. The method of claim 5 wherein the alkanol concentration is about 1.5 percent.

7. The method of claim 1 wherein the contacting and heating occur substantially simultaneously.

8. The method of claim 1 wherein the suspension of thawed cells is diluted into tris buffer.

9. The method of claim 1 wherein the protein is a mature eukaryotic protein.

10. The method of claim 1 wherein the cell is *E. coli* and the protein is mature human growth hormone.

11. The method of claim 1 wherein the cell is immediately cooled below 20° C. after step (a).

12. A method for the recovery of periplasmic proteins from a bacterial cell, comprising
   (a) contacting the cell with an effective amount of a lower alkanol having between two to four carbon atoms for a time and at a temperature sufficient to kill the cell without lysing the inner membrane;
   (b) cooling the cell to a temperature lower than about 20° C.; and
   (c) recovering the perplasmic protein from the remainder of the cell.

13. The method of claim 12 wherein the cell is cooled to a temperature sufficient to freeze the cell.

14. The method of claim 13 wherein the cell is first cooled to about −20° C. and then stored at about −80° C.

15. The method of claim 13 wherein separating periplasmic protein comprises thawing the cell, suspending it in aqueous buffer, centrifuging and recovering the supernatant fraction.

16. The method of claim 12 wherein the periplasmic protein is separated by centrifuging the cells and recovering the supernatant.

17. The method of claim 16 wherein the centrifuged cells are washed and the wash combined with the supernatant.

18. The method of claim 12 wherein the cell is not suspended in a hypertonic solution prior to cooling the cell in step (b).

19. The method of claim 12 wherein the cell is *E. coli* and the protein is mature human growth hormone.

20. The method of claim 12 wherein the cell is centrifuged to separate it from culture medium prior to cooling.

21. The method of claim 1 wherein the cell is not suspended in a hypertonic solution prior to cooling the cell in step (b).

22. A method for the recovery of a eukaryotic protein from the periplasmic space of a bacterial cell transformed to secrete the eukaryotic protein, comprising
   (a) contacting the cell with an effective amount of a lower alkanol having between two to four carbon atoms for a time and at a temperature sufficient to kill the cell without lysing the inner membrane;
   (b) causing the outer membrane of the cell to become permeable to passage of the periplasmic protein out of the cell; and
   (c) recovering the perplasmic proteins, including the eukaryotic protein, from the remainder of the cell.

23. A method for recovering protein from the periplasmic space of a bacterial cell transformed to secrete a eukaryotic protein comprising:
   (a) culturing the cell in a phosphate-limiting nutrient medium;
   (b) contacting the cell with an effective amount of a lower alkanol having between two to four carbon atoms for a time and at a temperature sufficient to kill the cell without lysing the inner membrane;
   (c) causing the outer membrane of the cell to become permeable to permit passage of the protein out of the cell; and
   (d) recovering the periplasmic proteins, including the eukaryotic protein, from the remainder of the cell.

24. The method of claim 23 wherein the culture medium contains less than about 1 mM of phosphate.

* * * * *